United States Patent [19]

Shimada et al.

[11] Patent Number: 5,329,058
[45] Date of Patent: Jul. 12, 1994

[54] PROCESS FOR PRODUCING ALKENYLBENZENE

[75] Inventors: Keizo Shimada, Iwakuni; Koji Sumitani, Koganei; Seiji Itoh, Iwakuni; Kazuhiro Sato, Matsuyama, all of Japan

[73] Assignee: Teijin Limied, Osaka, Japan

[21] Appl. No.: 949,471

[22] Filed: Oct. 23, 1992

[30] Foreign Application Priority Data

Apr. 25, 1990 [JP] Japan .................. 2-107659
Apr. 25, 1990 [JP] Japan .................. 2-107660
Dec. 18, 1991 [JP] Japan .................. 3-353178

[51] Int. Cl.$^5$ ............................... C07C 2/58
[52] U.S. Cl. ........................ 585/452; 585/438
[58] Field of Search .................. 585/438, 452

[56] References Cited

U.S. PATENT DOCUMENTS

| | | | |
|---|---|---|---|
| 3,244,758 | 4/1966 | Eberhardt | 260/668 |
| 3,766,288 | 10/1973 | Shima et al. | 260/668 |
| 3,953,535 | 4/1976 | Shima et al. | 585/452 |
| 4,018,840 | 4/1977 | Iwata et al. | 585/438 |
| 4,990,717 | 2/1991 | Sikkenga et al. | 585/452 |

FOREIGN PATENT DOCUMENTS

| | | |
|---|---|---|
| 0173335 | 3/1986 | European Pat. Off. . |
| 2291172 | 6/1976 | France . |
| 42-22474 | 11/1967 | Japan . |
| 56-34570 | 8/1981 | Japan . |
| 61-263643 | 11/1986 | Japan . |
| 62-263643 | 11/1986 | Japan . |
| 1269280 | 4/1972 | United Kingdom . |
| 2254802 | 10/1992 | United Kingdom . |
| 9116284 | 10/1991 | World Int. Prop. O. . |

*Primary Examiner*—Asok Pal
*Attorney, Agent, or Firm*—Wenderoth, Lind & Ponack

[57] ABSTRACT

In a process for producing an alkenylbenzene by the reaction of an alkylbenzene having 8 or more carbon atoms and a conjugated diolefin, the improvement in which the reaction is performed in the presence of a catalyst obtained by dispersing (a) an alkali metal and (b) potassium carbonate and/or potassium hydroxide in the presence of (c) an aromatic hydrocarbon having at least a substituent with a double bond.

11 Claims, No Drawings

PROCESS FOR PRODUCING ALKENYLBENZENE

This application is a continuation-in-part of international application PCT/JP91/00542, filed on Apr. 23, 1991, which designated the United States. This PCT application was published on Oct. 31, 1991 as WO 91/16284.

BACKGROUND OF THE INVENTION

1. Field of the Invention

This invention relates to a process for producing an alkenylbenzene efficiently in and safely by the reaction of an alkylbenzene and a conjugated diolefin in the presence of an alkali metal. More specifically, this invention relates to a process for producing an industrially useful alkenylbenzene. For example, 5-(o-tolyl)-pentene, an alkenylbenzene obtained by reacting o-xylene with 1,3-butadiene can be converted into naphthalenedicarboxylic acid which is useful as a high-molecular weight starting material by a reaction sequence in which 5-(o-tolyl)-pentene is cyclized into dimethyltetralin, and said dimethyltetralin is dehydrogenated into dimethylnaphthalene which is then oxidized into naphthalenedicarboxylic acid.

2. Description of Related Art

There has been so far known a process for producing an alkenylbenzene by the reaction of an alkylbenzene and 1,3-butadiene in the presence of an alkali metal (see U.S. Pat. No. 3,244,758).

The above process, however, suffers a defect that if an alkenylbenzene is obtained in high yield, costly metallic potassium has to be used in a large amount.

Further, in order to solve this problem, a process has been proposed in which when metallic potassium and metallic sodium are conjointly used as a catalyst in blowing 1,3-butadiene into an alkylbenzene for reaction, costly metallic potassium may be used in a small amount (see Japanese Patent Publication No. 34,570/1981 and U.S. Pat. Nos. 3,766,288 and 3,953,535).

Still further, an improved process has been proposed in which the reaction of o-xylene and butadiene is performed in a fixed bed with metallic potassium supported on potassium carbonate or alumina (U.S. Pat. No. 4,990,717).

These processes are, however, all processes directly using metallic potassium. Metallic potassium is highly reactive with air, oxygen, water, etc., fires only when contacting these substances and is a potential fire hazard. Especially, a sodium (Na-K) alloy is highly reactive with oxygen and water, burning on contact with traces of oxygen, water, etc., and being quite dangerous in the presence of inflammable substances (oils).

In British Patent No. 1,269,280, it is stated that in a side chain alkylation reaction of aromatics with olefins using sodium and an anhydrous potassium compound as a catalyst, a diene hinders the reaction.

Japanese Laid-open Patent Application (Kokai) No. 263,643/1986 involves a process in which toluene is alkenylated with butadiene using metallic sodium and anhydrous potassium sulfate as a catalyst.

SUMMARY OF THE INVENTION

It is an object of this invention to produce an alkenylbenzene in high yield, by solving the aforesaid problems, without directly using costly metallic potassium having a high risk of burning. Besides, this invention aims to produce an intended alkenylbenzene of high purity in high yield upon suppressing formation of complicated by-products hard to separate from the intended product by reacting an alkylbenzene with, e.g., 1,3-butadiene in the presence of a catalyst having high reactivity and high selectivity for an alkenylation reaction.

According to studies of the present inventors, it has been found that the object of this invention can be achieved by a process for producing an alkenylbenzene by the reaction of an alkylbenzene having 8 or more carbon atoms and a conjugated diolefin, wherein the reaction is performed in the presence of the following catalyst (i) or (ii):

(i) a catalyst obtained by dispersing (a) an alkali metal and (b) potassium carbonate and/or potassium hydroxide or (ii) a catalyst obtained by dispersing (a) an alkali metal and (b) potassium carbonate and/or potassium hydroxide in the presence of (c) an aromatic hydrocarbon having at least a substituent with a double bond.

This invention can provide an alkenylbenzene of high purity in high yield by suppressing formation of complicated by-products hard to separate from the intended product.

The process of this invention will be described in more detail below.

DESCRIPTION OF THE PREFERRED EMBODIMENTS (A) Starting materials

In the process of this invention, the alkenylbenzene is produced using the alkylbenzene having 8 or more carbon atoms and the conjugated diolefin as starting materials.

The alkylbenzene is one having 8 or more carbon atoms, preferably 8 to 10 carbon atoms. Examples of the alkylbenzene are ethylbenzene, o-xylene, m-xylene, p-xylene, ethyltoluene and diethylbenzene. These alkylbenzenes are properly selected depending on types of the intended alkenylbenzenes. It is advisable to use these alkylbenzenes singly. The reason is that when they are used in combination, the intended specific alkenylbenzene can scarcely be obtained in high purity from the reaction mixture.

For example, in the reaction of o-xylene and 1,3-butadiene, when other alkylbenzenes such as p-xylene, m-xylene, ethylbenzene, etc. are incorporated as impurities, purity of the intended product decreases notably. Accordingly, it is advisable that purity of o-xylene is not less than 95%, preferably not less than 98%. However, traces of hydrocarbons free from alkyl groups, such as benzene, cyclohexane, etc. may be incorporated.

Also in case of using ethylbenzene, m-xylene or p-xylene, purity of said alkylbenzene used singly is not less than 95%, preferably not less than 98%. Small amounts of hydrocarbons free from alkyl groups, such as benzene, cyclohexane, etc. may be incorporated.

It is advisable that the alkylbenzene used as a starting material in the reaction be dehydrated. Examples of dehydration are separation by adsorption with a suitable drying agent (e.g., activated alumina, silica gel, molecular sieves, and activated carbon), cryogenic separation, dehydration by previously contacting metallic sodium or metallic potassium. The lower water the content of the starting material the better. Especially preferable is a water content below the threshold amount measurable by a Karl Fischer method which is a usual method of measuring the water content, e.g., lower than several ppm.

Examples of the conjugated diolefin which is the other starting material used in this invention are butadiene and isoprene. 1,3-Butadiene may be prepared by any method, and any purity of 1,3-butadiene will do. For example, crude butadiene obtained by dehydrogenating butane or butene can be used as such, and 1,3-butadiene obtained by purifying said crude butadiene via extraction, etc. is also acceptable. It is advisable that 1,3-butadiene used in the reaction be dehydrated. Examples of dehydration are separation by adsorption with a suitable drying agent such as activated alumina, silica gel, molecular sieves or activated carbon, and cryogenic separation. The lower the water content of 1,3-butadiene the better. Especially preferable is the water content lower than several ppm.

(B) Catalyst and its preparation

As stated above, the reaction in the process of this invention is performed in the presence of the following catalyst (i) or (ii):

(i) a catalyst obtained by dispersing (a) an alkali metal and (b) potassium carbonate and/or potassium hydroxide or (ii) a catalyst obtained by dispersing (a) an alkali metal and (b) potassium carbonate and/or potassium hydroxide in the presence of (c) an aromatic hydrocarbon having at least a substituent with a double bond.

As the alkali metal (component (a)), sodium is preferable, and the higher the purity the better, but metals such as potassium, calcium, magnesium and aluminum may be contained in small amounts. Purity is not less than 90%, if possible, not less than 99%.

Meanwhile, component (b) is a dispersing agent of component (a). Potassium carbonate and/or potassium hydroxide can be used. It is advisable that they have been pretreated by calcination and dehydration at 200° C. to 500° C. for 2 to 30 hours.

Examples of potassium carbonate are potassium carbonates, potassium hydrogencarbonate and potassium sodium carbonate. They may contain small amounts of sodium carbonate, magnesium carbonate and calcium carbonate.

Potassium hydroxide obtained by calcination and dehydration is used; potassium hydroxide subjected to calcination and dehydration is preferably one having purity of not less than 80%. Ordinary pelletized sodium hydroxide has a water content of 10 to 15%. When said pelletized sodium hydroxide is dispersed as such with metallic sodium, a large amount of metallic sodium is decomposed and consumed, and catalytic activity is hardly developed. For this reason, it has to be dehydrated at a high temperature, preferably, 250° C. or above; however, it becomes liquid at about 150° C. and is hard to dry by dehydrogenation. In order to ease drying by dehydrogenation and develop high performance with a small amount of metallic sodium, it is mixed with inorganic oxides such as alumina and calcium silicate, calcined and dehydrated. Then, a calcined dehydrated inorganic composition containing excellent potassium carbonate is obtained.

Part of potassium hydroxide may be formed into potassium oxide via calcination and dehydration. Potassium hydroxide used to prepare the calcined dehydrated inorganic composition of potassium hydroxide may contain carbonates such as potassium carbonate, sodium carbonate, magnesium carbonate, calcium carbonate and barium carbonate. At times, containing suitable amounts of these carbonates helps exhibit higher performance.

Preferable component (b) is at least one compound selected from the group consisting of potassium carbonate, potassium hydrogencarbonate and sodium potassium carbonate.

Component (b) as a dispersing agent has an average particle size of preferably not more than about 100 micrometers, most preferably 10 to 50 micrometers.

When the aromatic hydrocarbon (component (c)) having at least a substituent with a double bond is used in the process of this invention, a catalyst having high activity can be obtained more advantageously. As component (c), an aromatic hydrocarbon having a conjugated double bond in a molecule is preferable. The conjugated double bond may be present either in the substituent or over the substituent and the aromatic ring (benzene ring) like styrene. Examples of component (c) are styrene, alpha-methylstyrene, beta-methylstyrene, vinyltoluene, divinylbenzene, indene, and alkylindene. Further examples of component (c) are 5-(o-tolyl)pentene in case of o-xylene as a starting material, 5-(p-tolyl)pentene in case of p-xylene, 5-(m-tolyl)pentene in case of m-xylene, and 5-phenylhexene in case of ethylbenzene.

A component (a):component (b) weight ratio in preparing the catalyst is 1:500 to 1:0.5, preferably 1:200 to 1:1, and more preferably 1:00–1:1. When the catalyst is prepared in the presence of component (c), it is advantageous to use component (c) in an amount of 0.01 to 20 mols, preferably 0.02 to 10 mols per mol of component (a).

It is advisable that the catalyst is prepared by dispersing components (a) and (b) in an inert solvent optionally in the presence of component (c) and the dispersion is carried out under an atmosphere of an inert gas such as nitrogen, helium, argon or hydrogen. The catalyst is prepared by a wet treating method to conduct dispersion and heat treatment in an inert solvent or a dry dispersion method in the absence of a solvent. The dry dispersion method is excellent from the aspect of activity of the catalyst, while the wet dispersion method is excellent from the aspect of handlability or safety in the production step.

The catalyst can be prepared by dispersing components (a) and (b) in the inert solvent optionally in the presence of component (c) with stirring at high speed.

For instance, when 3% by weight of metallic sodium is dispersed and supported on the dispersing agent such as potassium carbonate or the like, 3 parts of metallic sodium and 97 parts of potassium carbonate as the dispersing agent are simultaneously charged in 1,000 parts of o-xylene, and with stirring by heating at 130° to 160° C., 0.5 part of styrene is introduced to treat the mixture. It is also possible that a dispersion in a suitable dispersion mixing ratio is previously formed and an inert solvent is further added thereto, or potassium carbonate is charged and with dispersing, a diolefin is introduced to conduct activation by heating.

Examples of the inert solvent are paraffins having 8 to 20 carbon atoms and boiling at 100° to 230° C., preferably 130° to 200° C., such as n-octane, n-nonane, decane, undecane, and dodecane. Of these, alkylbenzenes used as the starting material are industrially preferable.

The reaction may be conducted in the presence of the thus uniformly dispersed catalyst by introducing the starting alkylbenzene and conjugated diolefin, e.g., 1,3-butadiene. If the pretreatment is conducted at 100° to 200° C. for 1 to 5 hours before the reaction in order to increase dispersibility of the starting alkylbenzene and the catalyst, activity can be improved.

As noted above, a carbonate may be present in dispersing components (a), (b) and (c). Examples of the carbonate are sodium carbonate, magnesium carbonate, calcium carbonate and barium carbonate. Alumina ($Al_2O_3$) is also acceptable.

(C) Reaction conditions and process

In the process of this invention, it is advisable that the reaction of the alkylbenzene and the conjugated diolefin is carried out in the substantial absence of moisture and oxygen, and that the starting materials introduced into the reaction system from outside, i.e., the alkylbenzene and the conjugated diolefin, are dehydrated as mentioned above.

Moreover, for oxygen or moisture to be substantially absent from the reaction system, it is advisable that a dry inert gas such as dry nitrogen or dry argon is filled in the space or, under a reaction condition above the boiling point of the alkylbenzene, a vapor of the alkylbenzene or the like is filled therein.

The alkali metal as component (a) can be used at any ratio per mol of the alkylbenzene. The ratio is usually not less than 1 mmols. When it is less than 1 mmols, the reaction undesirously becomes quite slow. When the ratio of the alkali metal to the alkylbenzene is too high, selectivity or yield of the intended product decreases at times. Accordingly, the upper limit is preferably not more than 300 mmols per mol of the alkylbenzene.

The amount of component (b) (potassium carbonate and/or potassium hydroxide) used in the process of this invention may be an amount required for 1 mmol or more of potassium ions per mol of the alkylbenzene. Usually, potassium carbonate and potassium hydroxide may be present in amounts of not less than 1 mmol, as potassium atom, per mol of the alkylbenzene. For these compounds to act as a dispersing agent, they are used in still larger amounts. For example, the amount of potassium carbonate is 1 to 500 mmols, as potassium atom, per mol of o-xylene.

When the amounts of potassium carbonate and potassium hydroxide are less than 1 mmol, the reaction is slow. When the amounts exceed 500 mmols, yield and selectivity of the end product become decreased. Accordingly, the range of the preferable amounts is 2 to 300 mmols.

In this invention, it is desirous that the reaction is performed at a temperature of 100° to 200° C. When the reaction temperature is lower than 100° C., the reaction time becomes long. When it exceeds 200° C., amounts of by-products become large. Both are thus unwanted. The desirous reaction temperature is 110° to 80° C. The molar ratio of the conjugated diolefin to the alkylbenzene can properly be selected within the ordinary conditions. For example, the alkylbenzene:conjugated diolefin molar ratio is 1:0.001 to 0.5, preferably 1:0.01 to 0.3, most preferably 1:0.05 to 0.2.

The reaction time is 0.05 to 10 hours. Said reaction time is related to the amount of the catalyst (g-catalyst/g-alkylbenzene), the catalyst composition (g-metallic sodium/g-potassium carbonate and/or potassium hydroxide), the reaction temperature (°C.) and the alkylbenzene:conjugated diolefin ratio (g-alkylbenzene/g-conjugated diolefin) respectively. A suitable time is employed in consideration of purity of the end product, mode of use of the catalyst, e.g., whether the catalyst is recycled or not, and so forth. Generally, the reaction time increases with a decrease in values of the above factors. It is preferably 0.2 to 10 hours, most preferably 0.3 to 5.

The reaction may be carried out by a batch method in which the alkylbenzene and the conjugated diolefin as the starting materials and the catalyst are simultaneously charged from the beginning to conduct the reaction, a semibatch method in which the alkylbenzene and the catalyst are first charged and a fixed amount of the conjugated diolefin is then introduced with the lapse of the reaction time, or a continuous method in which the alkylbenzene, the conjugated diolefin and the catalyst are continuously introduced into a reactor. A suitable combination of these methods is also available. Preferable is the semibatch method or the continuous method.

The continuous reaction includes two types, i.e., a method in which the reaction is conducted under dispersion and stirring of the catalyst into the reaction system while continuously feeding given amounts of the alkylbenzene and the conjugated diolefin, and a method in which the dispersed, activated catalyst is placed on a fixed bed and the continuous reaction is carried out while continuously feeding the alkylbenzene therein and introducing the conjugated diolefin into the alkylbenzene.

A tubular reactor, a column-type reactor or a tank-type reactor is available in the continuous reaction. The desirable system in the continuous reaction is a so-called cross flow continuous system in which a plurality of reaction zones are provided and a fixed amount of the conjugated diolefin is introduced in each of the reaction zones.

A reaction operation is not particularly limited if the alkylbenzene and the conjugated diolefin are well mixed in the presence of the catalyst. However, in a system of introducing the conjugated diolefin into the reaction system containing the catalyst, there is a tendency that a resinous or gummy substance presumed to be a conjugated diolefin polymer is adhered near the inlet of the conjugated diolefin to cause clogging. Accordingly, preferable is a system of introducing the conjugated diolefin and the alkylbenzene into the reaction system containing the catalyst in the form of a mixed phase of the conjugated diolefin and the alkylbenzene, e.g., a mixed liquid phase of a liquid conjugated diolefin and a liquid alkylbenzene, or a vapor-liquid mixed phase of a gaseous conjugated diolefin and a liquid alkylbenzene.

Alternatively, the clogging can be prevented by feeding the conjugated diolefin in the space of the reaction zone and conducting the absorption reaction in the surface of the reaction liquid containing the catalyst. Moreover, when a carrier gas is blown in introducing the conjugated diolefin, a stirring effect can be increased at the same time. Suitable examples of the carrier gas are inert gases with moisture and oxygen removed, such as nitrogen, argon and hydrogen.

Besides, the reaction can be preferably carried out with suitable stirring, while the conjugated diolefin is introduced in a vapor phase into the reaction system and the stirring effect can be also given with the gas. It is desirable that the stirring is carried out in a degree necessary for uniformly dispersing the catalyst into the reaction system and uniformly mixing the reaction starting materials with the reaction product.

In case of the reaction in the liquid phase dispersion reaction system, the catalyst used may be separated from the reaction mixture after the reaction by, for example, known means such as centrifugal sedimentation, gravity sedimentation, etc., or known means of separation from a liquid-solid phase at lower temperatures, such as filtration, centrifugal separation, etc. The separated catalyst can be recycled to the reaction system and reused.

When the catalyst is deactivated and the catalytic activity is lost, the alkali metal is deactivated on the phase of the surface of the dispersing agent. Accordingly, the catalyst with the organic substances adhered can be oxidized, calcined, regenerated and then reused.

According to the process of this invention, 5-(o-tolyl)pentene is formed by the reaction of o-xylene and 1,3-butadiene, 5-(p-tolyl)pentene by the reaction of p-xylene and 1,3-butadiene, 5-(m-tolyl)pentene by the reaction of m-xylene and 1,3-butadiene, and 5-(phenyl)-hexene by the reaction of ethylbenzene and 1,3-butadiene.

(D) Utilization of the alkenylbenzene

The alkenylbenzene, the intended product of this invention, as stated above, can be converted into a monoalkylnaphthalene or a dialkylnaphthalene which is a compound useful as a starting material of a drug or a high-molecular weight material by cyclizing and then dehydrogenating it. On this occasion, purity of pentene or hexene in cyclizing phenyl-hexene or tolyl-pentene becomes an issue.

Namely, the olefinic double bond in arylalkenes (main intended products) such as phenylhexenes and tolylpentenes is in the 1- or 2-position. In the usual method, isomers different in position of the olefinic double bond are secondarily formed and incorporated in considerable amounts. For example, in the reaction of o-xylene and 1,3-butadiene, 5-(o-tolyl)pentene-(1), and 5-(o-tolyl)-pentene-(2), are formed as intended products and 5-(o-tolyl)-pentene-(3) and 5(o-tolyl)pentene-(4) are formed as by-products.

Also in the other phenylhexene and tolylpentene formed by the reaction of ethylbenzene, p-xylene and m-xylene with 1,3-butadiene, isomers different in position of the olefinic double bond are secondarily formed and incorporated.

Of the above isomers, those having the olefinic double bond in the 1- or 2-position can be cyclized and converted into alkyltetralins, but the others cannot be converted into alkyltetralins, and are reacted with the intended alkyltetralins to form high-boiling products, decreasing the yield of the intended products.

Besides, it is quite hard to remove isomers having the olefinic double bond in the 3- or 4-position from the intended alkenylbenzenes in the process of this invention. For example, even if a reaction mixture of o-xylene and 1,3-butadiene [end products are 5-(o-tolyl)-pentene-(2) and 5-(o-tolyl)pentene-(1)] is roughly rectified and the resulting product is rectified at a reflux ratio of 20 with a rectification column having 50 steps in theoretical number, the isomers can scarcely be separated. On the contrary, the reaction product obtained by the process of this invention hardly contains such hard to separate by-products, and yields of the cyclization reaction products are extremely high.

The alkenylbenzenes can be converted into alkyltetralins by a method known per se, i.e., cyclization in contact with an acid catalyst such as sulfuric acid, solid phosphoric acid or silica alumina at a temperature of 100° to 250° C. for 10 seconds to 10 hours.

The alkyltetralins can be converted into alkylnaphthalenes by a method known per se, i.e., dehydrogenation in contact with a dehydrogenation catalyst such as alumina-chromia or $Pt/Al_2O_3$ at a temperature of 350° to 450° C. for 5 seconds to 10 hours.

The alkylnaphthalenes can be isomerized by a method known per se, i.e., contacting a solid acid catalyst such as silica-alumina, ZSM-5, Y-zeolite, H-mordenite or the like at a temperature of 200° to 450° C. for 5 seconds to 10 hours. For example, 1,5-dimethylnaphthalene can be converted into 2,6-dimethylnaphthalene.

According to the process of this invention, dimethylnaphthalene, a compound useful as a starting material of a high-molecular weight compound can be produced from the alkylbenzene as follows.

Namely, for example, o-xylene and 1,3-butadiene are reacted in the presence of the catalyst obtained by dispersing the alkali metal and potassium carbonate and/or potassium hydroxide optionally in the presence of the aromatic hydrocarbon having the double bond in the side chain to form 5-(o-tolyl)pentene. Then, said 5-(o-tolyl)pentene is cyclized in a manner known per se to form 1,5-dimethyltetralin. Subsequently, said 1,5-dimethylnaphthalene is isomerized into 2,6-dimethylnaphthalene.

Further, said 2,6-dimethylnaphthalene is oxidized into naphthalene-2,6-dicarboxylic acid.

The reaction products obtained by the process of this invention hardly contain hard to separate by-products, and yields of cyclization reaction products are therefore quite high.

In accordance with the process of this invention, an end product of high purity can be produced in high yield without directly using a costly metallic sodium-potassium (Na-K) alloy having a high risk of burning by suppressing formation of complicated by-products hard to separate from the intended product by reacting the alkylbenzene with the conjugated diolefin in the presence of the catalyst obtained by dispersing the alkali metal and potassium carbonate and/or potassium hydroxide fine particles optionally in the presence of the aromatic hydrocarbon having at least the substituent with the double bond.

The catalyst used in this invention has merits that unlike Na-K, it is easy to separate after the preparation or the reaction and is less costly.

Especially, when using the catalyst obtained by dispersing components (a), (b) and (c) in this invention, such advantages are achieved that activity of the catalyst becomes much stabler than the catalyst free from component (c), and the end product can be produced in high yield and in high concentration.

EXAMPLES

The following Examples illustrate this invention more specifically. However, this invention is not limited to such Examples.

In said Examples, yield and purity of the end product are defined as follows. Moreover, parts in said Examples are all by weight.

Yield and purity:

After the whole reaction mixture was filtered at room temperature, about 500 g of the reaction mixture was distilled with a Widmer spiral under reduced pressure of 22 mmHg (abs), and divided into a fraction having a spiral top temperature of lower than 75° C., a fraction of 75° to 170° C. and the remainder. The fraction of 75° to 170° C. was collected as a product obtained by alkenylating xylene with 1,3-butadiene. The yield of the alkenylated product in the whole reaction mixture was found from the proportion of the fraction of the alkenylated product occupied in the sample.

The yield of the end product was calculated by analyzing the fraction of the alkenylated product via gas chromatography and finding the contents of 5-(tolyl)-pentene (2) and 5-(tolyl)pentene (1). The fraction of the alkenylated product contained only less than 0.1% by weight of unreacted xylene.

The yield given when using xylene and ethylbenzene as alkylbenzenes was calculated by the following equation. Incidentally, the amount of 1,3-butadiene fed is not the amount of 1,3-butadiene reacted, but the amount of 1,3-butadiene fed to the reaction vessel. A part thereof therefore flows outside the system.

$$\text{Yield} = \frac{\text{Amount of an end product (g)}}{\text{Amount of 1,3-butadiene fed (g)}} \times \frac{54 \text{ (molecular weight of 1,3-butadiene)}}{160 \text{ (molecular weight of an end product)}} \times 100$$

EXAMPLE 1

(A) Preparation of a Finely Divided Dispersion of Metallic Sodium

Dry high-purity nitrogen (an oxygen content—not more than 1 ppm, a water content—not more than 0.1 ppm) was blown into 500 parts of substantially moisture-free o-xylene heat-refluxed previously in the presence of metallic sodium, distilled and further dehydrated with molecular sieves. After dissolved oxygen was removed, 2.5 parts of metallic sodium (purity 99.9%) were charged, and the mixture was emulsified and dispersed with an emulsifying/dispersing device at 110° to 120° C. for 30 minutes under the nitrogen atmosphere to prepare an emulsified dispersion of metallic sodium.

(B) Preparation of a Dispersing Agent and a Dispersion (B-1) Preparation of Potassium Carbonate and Its Dispersion A flask was charged with 100 parts of high-purity potassium carbonate (potassium carbonate, potassium hydrogencarbonate, sodium carbonate and potassium sodium carbonate: purity—99.9% or higher) obtained by calcining and dehydrating commercial high-purity potassium carbonate (purity 99.9% or higher) at 200° to 450° C. for 5 hours, and conducting cooling and pulverization to an average particle size of not more than 100 micrometers, and dried at 200° to 250° C. in a nitrogen atmosphere. Five hundred parts of the above dehydrated o-xylene were charged therein, and they were dispersed with an emulsifying/dispersing device for 30 minutes to form a dispersion of potassium carbonate.

(B-2) Preparation of a Potassium Hydroxide/alumina Dispersing Agent and Its Dispersion Twenty five parts of potassium hydroxide having reagent special grade purity of 85% (a 15% remainder—water) were dissolved in 80 parts of water, and 80 parts of an alumina fine powder calcined at 450° C. for 5 hours were charged and dipped therein. After water was evaporated to dryness at 100° to 150° C., the product was calcined and dried at 400° to 450° C. for 10 hours, cooled, and pulverized to an average particle size of 100 micrometers to obtain 100 parts of a 20% potassium hydroxide-on-alumina dispersion. The dispersion was further dried at 250° C. in a flask in a nitrogen atmosphere, and 500 parts of said dehydrated o-xylene were charged therein. The mixture was dispersed with an emulsifying/dispersing device for 30 minutes to form a potassium hydroxide-on-alumina dispersion. This dispersion was used in Examples 8 and 15.

(C) Preparation of a Metallic Sodium Catalyst Dispersion

The finely divided dispersion of metallic sodium prepared in (A) was mixed with the potassium carbonate dispersion prepared in (B-1) under stirring at high speed. Further 4.6 mols, per mol of metallic sodium, of styrene as an aromatic hydrocarbon (component (c)) were charged. The mixture was heated to 144° C. with stirring. Activation was conducted by heating at said temperature for 1 hour to form a catalyst dispersion.

(D) Synthesis Reaction of 5-(o-tolyl)pentene

The catalyst dispersion prepared in (C) was stirred at 140° to 145° C. for 1 hour. Then, 0.1 mol, per mol of o-xylene, of 1,3-butadiene was introduced, and the reaction was run.

After the reaction was over, the reaction mixture was rapidly cooled to 100° C. Subsequently, while maintaining the temperature at 100° C., stirring was stopped, and the reaction mixture was left to stand for 30 minutes and divided into the catalyst and the end product liquid phase. The end product, 5-(o-tolyl)-pentene was distilled under reduced pressure of 22 mmHg (obs), and yield and purity of 5-(o-tolyl)pentene were found with the results shown in Table 1.

EXAMPLES 2 to 8

Example 1 was repeated except that the catalyst composition, the aromatic hydrocarbon (component (c)), the reaction temperature and the reaction time were changed as shown in Table 1. The results are shown in Table 1.

TABLE 1

| | Catalyst | | | Aromatic hydrocarbon (component (c)) | | Reaction conditions | | 5-o-TP***** | | |
|---|---|---|---|---|---|---|---|---|---|---|
| | Amount of* Na (component (a)) (part by weight) | Inorganic composition (component (b)) Type** | Amount used (parts by weight)*** | Type | Amount used**** (mols) | Temp. °C. | Time hr. | Concentration in a reaction liquid wt. % | Yield % | Purity % |
| Example 1 | 0.5 | $K_2CO_3$ | 20 | Styrene | 4.6 | 140–145 | 2.0 | 12.8 | 88.9 | 99.0 |
| Example 2 | 0.6 | $K_2CO_3$ | 16 | Styrene | 5.7 | 143–146 | 2.0 | 12.8 | 89.0 | 99.1 |
| Example 3 | 0.4 | $KHCO_3$ | 25 | Styrene | 6.9 | 140–146 | 2.0 | 12.8 | 88.8 | 99.0 |

TABLE 1-continued

| | Catalyst | | | Aromatic hydrocarbon (component (c)) | | Reaction conditions | | 5-o-TP***** | | |
|---|---|---|---|---|---|---|---|---|---|---|
| | Amount of* Na (component (a)) (part by weight) | Inorganic composition (component (b)) | | | | | | Concentration in a reaction liquid wt. % | Yield % | Purity % |
| | | Type** | Amount used (parts by weight)*** | Type | Amount used**** (mols) | Temp. °C. | Time hr. | | | |
| Example 4 | 0.8 | KNa₂CO₃ | 12 | α-Methyl-styrene | 4.3 | 140 | 2.0 | 12.8 | 88.9 | 99.1 |
| Example 5 | 0.5 | K₂CO₃ | 20 | Vinyl-toluene | 5.9 | 144–145 | 2.0 | 12.7 | 88.6 | 98.9 |
| Example 6 | 0.6 | K₂CO₃/Na₂CO₃ (5/5) | 16 | Divinyl-benzene | 5.7 | 140–145 | 2.0 | 12.7 | 88.7 | 99.2 |
| Example 7 | 0.6 | K₂CO₃/KOH (9/1) | 16 | β-Methyl-styrene | 5.7 | 140–145 | 2.0 | 12.8 | 89.1 | 99.1 |
| Example 8 | 0.4 | KOH/Al₂O₃ (2/8) | 25 | Indene | 8.6 | 140–145 | 2.0 | 12.6 | 88.1 | 99.0 |

(Notes)
*: Amount per 200 parts by weight of o-xylene
**: The parenthesized value is weight ratio of components. For example, KOH/Al₂O₃ = (2/8) indicates a weight ratio of KOH and Al₂O₃ is 2:8
***: Amount used per part by weight of metallic Na
****: Amount used per mol of metallic Na
*****: 5-(o-tolyl)pentene

EXAMPLES 9 to 15

Example 1 was repeated except that the aromatic hydrocarbon (component (c)) was not used, and the catalyst composition, the reaction temperature and the reaction time were changed as shown in Table 2. The results are shown in Table 2.

and 1,3-butadiene fed to the reaction system is effectively reacted without flowing out of the system, contributing to formation of 5-(o-tolyl)pentene.

EXAMPLES 16 to 22

An alkenylation reaction with 1,3-butadiene was carried out as in Example 1 except that o-xylene was re-

TABLE 2

| | Catalyst | | | Aromatic hydrocarbon (component (c)) | | Reaction conditions | | 5-o-TP**** | | |
|---|---|---|---|---|---|---|---|---|---|---|
| | Amount of* Na (component (a)) (part by weight) | Inorganic composition (component (b)) | | | | | | Concentration in a reaction liquid wt. % | Yield % | Purity % |
| | | Type** | Amount used (parts by weight)*** | Type | Amount used (mols) | Temp. °C. | Time hr. | | | |
| Example 9 | 0.5 | — | 00 | — | — | 140–145 | 2.0 | 4.4 | 31.5 | 95.7 |
| Example 10 | 0.5 | K₂CO₃ | 20 | — | — | 140–145 | 2.0 | 10.3 | 73.5 | 96.8 |
| Example 11 | 0.4 | KHCO₃ | 25 | — | — | 140–145 | 2.0 | 8.9 | 63.2 | 97.1 |
| Example 12 | 0.3 | KNaCO₃ | 33 | — | — | 140–145 | 2.0 | 9.2 | 65.3 | 97.3 |
| Example 13 | 0.6 | K₂CO₃/Na₂CO₃ (5/5) | 16 | — | — | 140–145 | 2.0 | 9.7 | 68.3 | 97.2 |
| Example 14 | 0.6 | K₂CO₃/KOH (9/1) | 16 | — | — | 140–145 | 2.0 | 9.4 | 65.8 | 98.1 |
| Example 15 | 0.4 | KOH/Al₂O₃ (2/8) | 25 | — | — | 140–145 | 2.0 | 8.7 | 63.5 | 94.1 |

(Notes)
*: Amount per 200 parts by weight of o-xylene
**: The parenthesized value is a weight ratio of components. For example, KOH/Al₂O₃ = (2/8) indicates a weight ratio of KOH and Al₂O₃ is 2:8
***: Amount used per part by weight of metallic Na
****: 5-(o-tolyl)pentene From Tables 1 and 2, it is found that the catalyst is activated by a wet preparation method, and 5-(o-tolyl)-pentene of high purity is obtained in high yield.

It is also found that in using the aromatic hydrocarbon (component (c)), the concentration of 5-(o-tolyl)-pentene of the reaction liquid after the reaction is high, placed with p-xylene. Preparation of a catalyst and reaction were also carried out in the same way as in Example 1. The results are shown in Table 3. Said Table 3 reveals that according to this invention, 5-(p-tolyl)-pentene of high purity was obtained in high yield.

TABLE 3

| | Catalyst | | | Aromatic hydrocarbon (component (c)) | | Reaction conditions | | 5-o-TP***** | | |
|---|---|---|---|---|---|---|---|---|---|---|
| | Amount of* Na (component (a)) (part by weight) | Inorganic composition (component (b)) | | | | | | Concentration in a reaction liquid wt. % | Yield % | Purity % |
| | | Type** | Amount used (parts by weight)*** | Type | Amount used**** (mols) | Temp. °C. | Time hr. | | | |
| Example | 0.7 | K₂CO₃ | 14 | Styrene | 4.9 | 135–140 | 2.0 | 12.7 | 88.5 | 99.9 |

TABLE 3-continued

| | Catalyst | | | Aromatic hydrocarbon (component (c)) | | Reaction conditions | | 5-o-TP***** | | |
|---|---|---|---|---|---|---|---|---|---|---|
| | Amount of* Na (component (a)) (part by weight) | Inorganic composition (component (b)) | | | | | | Concentration in a reaction liquid wt. % | Yield % | Purity % |
| | | Type** | Amount used (parts by weight)*** | Type | Amount used**** (mols) | Temp. °C. | Time hr. | | | |
| Example 16 | 0.7 | K$_2$CO$_3$ | 14 | Indene | 4.9 | 135-140 | 2.0 | 12.7 | 88.2 | 99.0 |
| Example 17 | 0.7 | KHCO$_3$ | 14 | α-Methyl styrene | 3.9 | 135-140 | 2.0 | 12.6 | 87.8 | 98.8 |
| Example 18 | 0.7 | KNaCO$_3$ | 14 | Divinyl benzene | 3.9 | 135-140 | 2.0 | 12.6 | 88.0 | 99.1 |
| Example 19 | 0.7 | K$_2$CO$_3$/Na$_2$CO$_3$ (6/4) | 14 | β-Methyl styrene | 4.9 | 135-140 | 2.0 | 12.5 | 87.3 | 98.9 |
| Example 20 | 0.7 | K$_2$CO$_3$ | 14 | — | — | 135-140 | 2.0 | 9.6 | 67.3 | 98.1 |
| Example 21 | 0.7 | KHCO$_3$ | 14 | — | — | 135-140 | 2.0 | 9.4 | 66.1 | 98.2 |

(Notes)
*: Amount per 200 parts by weight of o-xylene
**: The parenthesized value is a weight ratio of components. For example, KOH/Na$_2$O$_3$ = (6/4) indicates a weight ratio of KOH and Na$_2$O$_3$ is 2:8
***: Amount used per part by weight of metallic Na
****: Amount used per mol of metallic Na
*****: 5-(o-tolyl)pentene

EXAMPLE 23

Synthesis of 5-(phenyl)hexene by the reaction of ethylbenzene and 1,3-butadiene

The alkenylation reaction was conducted with 1,3-butadiene using ethylbenzene instead of o-xylene.

The reaction mixture was treated, and 5-phenylhexene as an end product was distilled under reduced pressure of 25 mmHg (abs). Yield and purity were found to be 98.7% and 89.5%, respectively.

EXAMPLE 24

A catalyst was obtained as in Example 1 by dispersing and mixing a dispersion of metallic sodium, a dispersion of potassium carbonate and 5-(o-tolyl)pentene as an aromatic hydrocarbon compound having a double bond in a side chain (component (c)). Namely, 1,060 parts of starting o-xylene, 1.5 parts of metallic sodium, 3 parts of potassium carbonate and 20 parts of 5-(o-tolyl)pentene were stirred at 140° to 145° C. for 1 hour. Then, 54 parts of 1,3-butadiene were introduced over a period of 2 hours. The reaction was repeated four times under the same conditions as in Example 1. The results are shown in A-1 to A-4 of Table 4.

The reaction was run as above except that 5-(o-tolyl)pentene was not added. The results are shown in B-1 to B-4 of Table 4.

Table 4 reveals that in case of not adding 5-(o-tolyl)pentene, yield is low with much irregularity, compared to a case of adding 5-(o-tolyl)pentene.

By the way, the concentration (% by weight) of the end product in the reaction liquid is a value obtained by deducting the amount of 5-(o-tolyl)pentene added before the reaction.

TABLE 4

| | 5-(o-tolyl)pentene | | |
|---|---|---|---|
| | Concentration* | Yield (%) | Purity (%) |
| A-1 | 12.94 | 90.1 | 98.9 |
| A-2 | 12.83 | 89.3 | 99.1 |
| A-3 | 12.88 | 89.7 | 99.0 |
| A-4 | 12.91 | 90.0 | 98.9 |
| B-1 | 9.62 | 67.5 | 98.1 |
| B-2 | 9.04 | 63.1 | 98.7 |
| B-3 | 8.69 | 60.5 | 98.9 |
| B-4 | 9.31 | 65.1 | 98.5 |

*Concentration (wt. %) of 5-(o-tolyl)pentene in a reacton liquid after the reaction

EXAMPLE 25

2,6-Dimethylnaphthalene was formed by cyclization of 5-(o-tolyl)pentene, dehydrogenation or isomerization as follows.

(A) Formation of 1,5-Dimethyltetralin by Cyclization of 5-(o-tolyl)pentene

Using a 10% toluene solution of 5-(o-tolyl)-pentene having purity of 99.0% which was obtained in Example 1, cyclization was conducted in the presence of solid phosphoric acid as a catalyst at a reaction temperature of 150° to 200° C. in a nitrogen atmosphere. Conversion of the starting material was 100%, and selectivity to 1,5-dimethyltetralin which was the cyclized product was 95% or more.

(B) Formation of 1,5-Dimethylnaphthalene by Dehydrogenation of 1,5-Dimethyltetralin Using a 10% toluene solution of 1,5-dimethyltetralin obtained by the above method (A), dehydrogenation was conducted at 400° C. in a hydrogen atmosphere in the presence of a 0.3% Pt/Al$_2$O$_3$ catalyst for dehydrogenation to obtain 1,5-dimethylnaphthalene. Conversion of 1,5-dimethyltetralin was 100%, and selectivity to 1,5-dimethylnaphthalene was 97%.

(C) Formation of 2,6-Dimethylnaphthalene by Isomerization of 1,5-Dimethylnaphthalene 1.5-Dimethylnaphthalene obtained by dehydrogenation in (B) was isomerized into 2,6-dimethylnaphthalene as follows.

Using a 10% toluene solution of 1,5-dimethylnaphthalene, isomerization was conducted at a temperature of 350° to 400° C. in a nitrogen atmosphere in the presence of an alumina dispersion catalyst containing 30% of H-mordenite. As a result, there was obtained a mixture comprising 10% of 1,5-dimethylnaphthalene, 43% of 2,6-dimethylnaphthalene, 44% of 1,6-dimethylnaphthalene and 3% of the other naphthalene compounds. The mixture was crystallized and separated, and 50% of 2,6-dimethylnaphthalene having purity of 98% was recovered.

We claim:

1. In a process for producing an alkenylbenzene by the reaction of an alkylbenzene having 8 or more carbon atoms and a conjugated diolefin, the improvement in which the reaction is performed in the presence of a catalyst obtained by dispersing (a) metallic sodium and (b) compound selected from the group consisting of potassium carbonate, potassium hydrogen carbonate, potassium sodium carbonate, potassium hydroxide and mixtures thereof in the presence of (c) an aromatic hydrocarbon having at least a substituent with a double bond.

2. The process of claim 1 wherein the alkylbenzene is ethylbenzene, o-xylene, m-xylene or p-xylene.

3. The process of claim 1 wherein the conjugated diolefin is 1,3-butadiene.

4. The process of claim 1 wherein component (b) is particles having an average particle size of not more than about 100 micrometers.

5. The process of claim 1 wherein component (c) is an aromatic hydrocarbon having a conjugated double bond in a molecule.

6. The process of claim 1 wherein the dispersion is performed in an inert solvent.

7. The process of claim 6 wherein the inert solvent is an alkylbenzene having 8 or more carbon atoms.

8. The process of claim 1 wherein the dispersion is performed at such a temperature that the metal as component (a) can be melted.

9. The process of claim 1 wherein the dispersion is performed at a temperature of 100° to 230° C. under stirring.

10. The process of claim 1 wherein the dispersion is performed at a component (a):component (b) weight ratio of 1:500 and 1:0.5.

11. The process of claim 1 wherein the dispersion is performed using component (c) in an amount of 0.01 to 20 mols per mol of component (a).

* * * * *